United States Patent
Okuno et al.

(10) Patent No.: US 6,607,718 B1
(45) Date of Patent: Aug. 19, 2003

(54) HAIR COSMETIC COMPOSITION

(75) Inventors: Mika Okuno, Tokyo (JP); Kaori Kojima, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/489,921

(22) Filed: Jan. 24, 2000

(30) Foreign Application Priority Data

Jan. 26, 1999 (JP) .......................................... 11-017601

(51) Int. Cl.⁷ ................................................ A61K 7/06
(52) U.S. Cl. ................ 424/70.13; 424/70.1; 424/70.11; 424/70.19; 424/70.27; 424/70.31
(58) Field of Search ................................ 424/401, 70.1, 424/70.11, 70.19, 70.13, 70.27, 70.28, 70.31

(56) References Cited

U.S. PATENT DOCUMENTS

| | | | |
|---|---|---|---|
| 4,159,316 A | | 6/1979 | Januszewski et al. |
| 5,051,252 A | * | 9/1991 | Schultz et al. |
| 5,104,646 A | * | 4/1992 | Bolich et al. |
| 5,538,720 A | * | 7/1996 | Jendryssek-Pfaff et al. ...... 424/70.1 |

FOREIGN PATENT DOCUMENTS

| | | |
|---|---|---|
| EP | 0 027 730 | 4/1981 |
| GB | 2 205 743 | 12/1988 |

OTHER PUBLICATIONS

Patent Abstracts of Japan, Hiroko TSUDA, et al., "Transparent or Semitransparent Hair Preparations Containing Surfactants, Oils and/or Fats, and Water–soluble Alcohols", JP03223208, Oct. 2, 1991, XP–002229243.

* cited by examiner

Primary Examiner—Thurman K. Page
Assistant Examiner—Brian K. Seidleck
(74) Attorney, Agent, or Firm—Oblon, Spivak, McClelland, Maier & Neustadt, P.C.

(57) ABSTRACT

A composition that is suitable for treating hair includes: (A) 40 to 98 wt. % of a polyhydric alcohol; (B) at least one component, soluble in component (A), selected from the group consisting of a fat, an oil, a nonionic surfactant, a cationic surfactant, a higher alcohol, a hydroxycarboxylic acid, a dicarboxylic acid, an aromatic carboxylic acid, urea, guanidine and an aromatic alcohol and mixtures thereof; (C) 0 to 20 wt. % of water; and (D) 0.3 to 10 wt. % of hydroxypropyl cellulose.

12 Claims, No Drawings

HAIR COSMETIC COMPOSITION

BACKGROUND OF THE INVENTION

1. Field of the Invention

This invention relates to an easy to handle hair cosmetic composition that acts on the hair and is rinsed off after application.

2. Discussion of the Background

Japanese Patent Application Laid-Open No. HEI 3223208 describes a hair treatment composition that combines a cationic surfactant, a nonionic surfactant, a fat or oil, and a water soluble alcohol. This composition forms liquid crystals when diluted with 2 to 30 times the amount of water. Although the surfactants and the fat or oil in the above-described composition remain on the hair, its effects on the hair are not sufficient because the low viscosity of the liquid makes handling difficult. In addition, effects are exhibited only when the hair treatment composition forms liquid crystals when diluting with 2 to 30 times the amount of water.

SUMMARY OF THE INVENTION

An object of the present invention is therefore to provide a composition which can be handled easily and acts efficiently on the hair thereby making the hair pleasant to touch, improving appearance and the like, and is easily rinsed off after application.

The inventors have found, surprisingly, that a hair cosmetic composition prepared by dissolving a component in a system rich in a polyhydric alcohol with hydroxypropyl cellulose as a thickener is easy to handle and acts efficiently on the hair, thereby providing the hair with good touch, feel, appearance and the like. They have also found that since such a hair cosmetic composition generates heat upon mixing with water when rinsed after application, the effects of the component which acts on the hair are heightened.

The objects of this invention are attained by providing a composition that includes:

(A) 40 to 98 wt. % of a polyhydric alcohol;

(B) at least one component, soluble in component (A), selected from the group consisting of fats, oils, nonionic surfactants, cationic surfactants, higher alcohols, hydroxycarboxylic acids, dicarboxylic acids, aromatic carboxylic acids, urea, guanidines and aromatic alcohols and mixtures thereof;

(C) 0 to 20 wt. % of water; and (D) 0.3 to 10 wt. % of hydroxypropyl cellulose.

The composition according to the present invention acts efficiently on the hair and can be easily handled.

DETAILED DESCRIPTION OF THE INVENTION

As the component (A), polyhydric alcohols in the liquid form at normal temperature and pressure are preferred, with those having 2 to 8 carbon atoms in total being more preferred. Specific preferred examples include ethylene glycol, propylene glycol, 1,2-butylene glycol, 1,3-butylene glycol, 3-methyl-1,3-butylene glycol, dipropylene glycol, hexylene glycol, glycerin, trimethylol propane, pentaerythritol, xylitol, sorbitol and mannitol.

Polyhydric alcohols can be used either singly or in combination. The amount of the polyhydric alcohol is desirably 40 to 98 wt. % (which will hereafter be called "%" or "wt. %" and is defined as the weight % of a component with regard to the weight of the whole composition) of the hair cosmetic composition. Such a large amount permits the dissolution of the component (B) in the component (A) and thereby efficient exhibition of the effects of the component (B) on the hair, with 50 to 95 wt. % being more preferred and 60 to 90 wt. % being particularly preferred. These ranges include all values and subranges therebetween.

The component (B) which acts on the hair is a component which is different from the polyhydric alcohol (A) and is soluble in the polyhydric alcohol, thereby providing the hair with good touch, feel (moisturized feeling, smoothness), pliability and appearance such as luster. Preferred examples of the component mainly for imparting the hair with a moisturized feel and an improved pliability include fats and oils, and nonionic surfactants.

Component (B), which is soluble in component (A), can be selected from the group consisting of fats, oils, nonionic surfactants, cationic surfactants, higher alcohols, hydroxycarboxylic acids, dicarboxylic acids, aromatic carboxylic acids, urea, guanidines and aromatic alcohols, and mixtures thereof.

Preferred examples of the fats and oils include higher alcohols having a linear or branched $C_{8-24}$ alkyl or alkenyl group; hydrocarbon oils such as liquid paraffin, Vaseline and solid paraffin; lanolin derivatives such as liquid lanolin and lanolin fatty acid esters; higher fatty acid esters having 8 to 24 carbon atoms; higher fatty acids having 8 to 24 carbon atoms; polyoxyethylene alkyl ethers containing not more than 5 moles of POE such as polyoxyethylene (3 moles) cetyl ether; animal and vegetable fats and oils such as mink oil and olive oil; cholesterol fatty acid esters; di- and triglycerides; and silicon oils such as dimethyl polysiloxane. Among the above-exemplified fats and oils, the higher alcohols, higher fatty acid esters and polyoxyethylene alkyl ethers are more preferred, with the higher alcohols being particularly preferred.

Preferred examples of the nonionic surfactant include monoglycerides such as sorbitan fatty acid esters and glycerin monooleates; glyceryl ethers such as glyceryl $C_{8-24}$ alkyl ethers; and polyether-modified silicones such as dimethyl polysiloxane polyoxyalkylene copolymer. Among them, those having an HLB not greater than 10 are preferred from the viewpoint of touch feeling. More preferably those having an HLB of not greater than 9, and most preferably those having an HLB of not greater than 7 are also suitable. These ranges include all values and subranges therebetween.

Preferred examples of the component (B) for improving the smoothness of the hair include cationic surfactants, of which quaternary ammonium salts are preferred, such as linear alkyl trimethylammonium halides, linear dialkyl dimethylammonium halides, branched alkyl trimethylammonium halides, linear dialkylammonium halides and branched dialkyl dimethylammonium halides. The linear or branched alkyl group preferably has 8 to 24 carbon atoms. More preferred examples include cetyl trimethylammonium halides, stearyl trimethylammonium halides, behenyl trimethylammonium halides and dicetyl dimethylammonium halides. Preferred examples of the counter ions of these quaternary ammonium salts include chloride ions, bromide ions and iodide ions.

Preferred examples of the component (B) for providing the hair with luster include hydroxycarboxylic acids such as α-hydroxy acid and β-hydroxy acid; dicarboxylic acids such as 1,2-dicarboxylic acid and 1,3-dicarboxylic acid, aromatic carboxylic acids, urea, guanidines and aromatic alcohols.

Preferred examples of the hydroxycarboxylic acid include glycolic acid, lactic acid, methyl lactic acid, mandelic acid, 4-hydroxymandelic acid, 3-hydroxy-4-methoxymandelic acid, 4-hydroxy-3-methoxymandelic acid, 3-(2-hydroxyphenyl) lactic acid, 3-(4'-hydroxyphenyl)lactic acid, 3,4-dihydroxymandelic acid, glyceric acid, malic acid, tartaric acid and citric acid. Preferred examples of the dicarboxylic acid include malonic acid, succinic acid, maleic acid and fumaric acid. Preferred examples of the aromatic carboxylic acid include benzoic acid, phthalic acid and salicylic acid. Among them, malic acid, succinic acid and maleic acid are most preferred.

It is more preferred to add at least one component (B) selected from the above-described higher alcohols, nonionic surfactants, cationic surfactants and hydroxycarboxylic acids. These components (B) can be used either singly or in combination. No limitation is imposed on the amount of the component (B) insofar as it can provide good touch feeling and appearance to the hair. Preferably, however, component (B) is added in an amount ranging from 0.01 to 40%, more preferably 0.05 to 30%, most preferably 0.1 to 25%. These ranges include all values and subranges therebetween.

When the hair cosmetic composition of the present invention is used, water as the component (C) will react with a polyhydric alcohol, component (A), and generate heat, thereby heightening the effects of the component (B) that acts on the hair. From such a viewpoint, an amount of water as small as possible is preferred. Preferably, water is added in an amount of 0 to 20%, more preferably 1 to 10% and particularly preferably 2 to 5%. These ranges include all values and subranges therebetween.

In the present invention, hydroxypropyl cellulose is employed as the thickener (D). A large number of thickeners suitable for use in a cosmetic composition are known, but in the system of the present invention, hydroxypropyl cellulose is desired because it has excellent solubility in component (A) and thickening can be provided without damaging the touch feeling. The hydroxypropyl cellulose having a viscosity of 100 to 4000 mPa.s as measured at 20° C. in a 2% aqueous solution is preferred from the viewpoint of thickening efficiency, of which that having a viscosity of 200 to 3500 mPa.s is more preferred. These ranges include all values and subranges therebetween.

The hydroxypropyl cellulose (D) is added in an amount of 0.3 to 10%, with 0.5 to 5% being particularly preferred. These ranges include all values and subranges therebetween.

To the hair cosmetic composition of the present invention, a perfume, antiseptic, colorant, pH regulator, ultraviolet absorber, antioxidant and/or protein derivative can be also added. The system of the hair cosmetic composition according to the present invention is particularly preferred to have a pH of 2 to 7, with pH 2.5 to 5 being more preferred. These ranges include all values and subranges therebetween.

Preferably, the hair cosmetic composition of the present invention is rinsed after application to the hair and it is used, for example, as a hair rinse, hair conditioner, hair treatment or hair pack. More preferably, the hair cosmetic composition of the present invention is rinsed after a proper amount is taken in hand and then applied to the hair or after a proper amount is applied directly to the hair from its container. It is also possible to apply the hair cosmetic composition of the present invention to the hair by hand or directly from its container, followed by application of another hair rinse, hair conditioner or the like. This makes it possible not only to bring about the effects of the hair cosmetic composition of the present invention, but also to heighten the effects of another hair rinse, hair conditioner or the like. In this manner, the component (B) in the hair cosmetic composition of the present invention can easily be applied to the hair due to the appropriate viscosity of the composition and it therefore acts on the hair efficiently. When the hair cosmetic composition is rinsed away with water, the component (A) reacts with the water and the temperature of the cosmetic composition rises, which improves the action of the component (B) on the hair. Accordingly, it is preferred, when the cosmetic composition of the present invention is mixed in the same amount of water (so as to set their ratio at 1:1) having the same temperature, to adjust the amount of the component (A) so as to increase the water temperature by at least 2° C.

EXAMPLES

Having generally described this invention, a further understanding can be obtained by reference to certain specific examples which are provided herein for purposes of illustration only, and are not intended to be limiting unless otherwise specified.

Example 1

Components for each of the hair cosmetic compositions shown in Table 1 were mixed. The organoleptic comparison among the resulting hair cosmetic compositions in handling ease and smoothness, moisturized touch, styling ease and luster of the hair was conducted by a panel of 10 female experts and the results were evaluated in accordance with the below-described standards. It should be noted that upon organoleptic comparison, the panel of 10 female experts used each of those compositions by taking 8 g of it in hands, applying it to the moisturized hair and then rinsing it off with water.

Handling Ease
  It can be handled easily because it is free from dripping from the hands and easily applicable to the hair: +1
  It is difficult to compare: 0
  Dripping of it from the hands prevents smooth application and therefore it cannot be handled easily: −1
Smoothness
  The hair is smooth and sleek: +1
  It is difficult to compare: 0
  The smoothness of the hair is insufficient: −1
Moisturized Feeling
  Moisturized feeling is imparted to the hair: +1
  Difficult to compare: 0
  Moisturized feeling is not imparted to the hair: −1
Styling Ease of the Hair
  The hair is styled well without disordered hair: +1
  It is difficult to compare: 0
  The hair is not styled well with much disordered hair: −1
Luster of the Hair
  The hair has luster: +1
  It is difficult to compare: 0
  The hair lacks luster: −1
  When the total points of all the experts were four or greater, the composition was evaluated as A; when the total points were 3 to −3, the composition was evaluated as B; and when the total points were −4 or less, the composition was judged C.

Example 2

As a result of mixing each of the invention products 1 to 3 with the same amount of water having the same temperature, a temperature rise by at least 2° C. was recognized.

Example 3

Each of the invention products 1 to 3 was taken in hands and then applied to the moisturized hair. A commercially available hair rinse was applied thereto, followed by rinsing away with water. As a result, the similar effects to Example 1 were exhibited and at the same time, the effects of the hair rinse were heightened.

As is apparent from Examples 1 to 3, the composition according to the present invention that includes a large amount of a polyhydric alcohol, a component acting on the hair, a small amount of water to be added optionally and hydroxypropyl cellulose is excellent in any one of handling ease, smoothness, moisturized feeling, styling ease and luster of the hair, compared with the similar composition except that the amount of the polyhydric alcohol is small or except that another thickener is employed.

TABLE 1

Amount of components (A), (B), (C), and (D) (in wt. %) and results of testing.

|  | Invention product | | | Comparative product | | | |
| --- | --- | --- | --- | --- | --- | --- | --- |
|  | 1 | 2 | 3 | 1 | 2 | 3 | 4 |
| (A) | Balance | Balance | Balance | Balance | Balance | Balance | Balance |
| Dipropylene glycol |  |  |  |  |  |  |  |
| 1,3-Butylene glycol | — | — | 40 | — | — | — | — |
| (B) |  |  |  |  |  |  |  |
| Cetyl alcohol | 5.0 | 5.0 | 5.0 | 5.0 | 5.0 | 5.0 | 5.0 |
| Isostearyl glyceryl ether <HLB 2.7> | 3.0 | 3.0 | 4.0 | 3.0 | 3.0 | 3.0 | 3.0 |
| Beheny trimethylammonium chloride | 2.0 | 2.0 | 2.0 | 2.0 | 2.0 | 2.0 | 2.0 |
| Malic acid | 1.5 | 1.5 | 0.5 | 1.5 | 1.5 | 1.5 | 1.5 |
| (C) |  |  |  |  |  |  |  |
| Water | — | 5 | — | — | 5 | — | 80 |
| (D) |  |  |  |  |  |  |  |
| Hydroxylpropyl cellulose (265) | 1.5 | 1.5 | 1.0 | — | — | — | 1.0 |
| Hydroxypropyl cellulose (2880) | — | — | 1.0 | — | — | — | 1.0 |
| Hydroxyethyl cellulose | — | — | — | 1.5 | 1.5 | — | — |
| pH regulator (KOH) | q.s. | q.s. | q.s. | q.s. | q.s. | q.s. | q.s |
| Handling ease | A | A | A | C | C | C | C |
| Smoothness | A | A | A | C | C | C | C |
| Moisturized feeling | A | A | A | C | C | C | C |
| Styling ease | A | A | A | C | C | C | C |
| Luster | A | A | A | B | B | B | B |

The numeral in the parentheses after the words "Hydroxypropyl cellulose" indicates the viscosity as measured at 20° C. as a 2% aqueous solution.

The priority document of the present application, Japanese Patent Application No. 11-017601, filed Jan. 26, 1999, is incorporated herein in its entirety by reference.

Obviously, numerous modifications and variations on the present invention are possible in light of above teachings. It is therefore to be understood that within the scope of the appended claims, the invention may be practiced otherwise than as specifically described herein.

What is claimed is:

1. A hair cosmetic composition, consisting essentially of:
    (A) 40 to 98 wt. % of a polyhydric alcohol is selected from the group consisting of ethylene glycol, propylene glycol, 1,2-butylene glycol, 1,3-butylene glycol, 3-methyl-1,3-butylene glycol, dipropylene glycol, hexylene glycol, glycerin, trimethylol propane, pentaerythritol, xylitol, sorbitol, and mannitol and mixtures thereof;
    (B) 0.01 to 40% of at least one component, soluble in component (A), selected from the group consisting of a fat, nonionic surfactant, a cationic surfactant, a higher alcohol, a hydroxycarboxylic acid, a dicarboxylic acid and mixtures thereof;
    (C) 0 to 20 wt. % of water; and
    (D) 0.3 to 10 wt. % of hydroxypropyl cellulose,
    wherein a temperature of said composition rises by at least 2° C. when mixed with the same amount of water having the same initial temperature.

2. The composition according to claim 1, wherein a 2 wt. % aqueous solution of said hydroxypropyl cellulose (D) has a viscosity of 100 to 4000 mPa.s at 20° C.

3. The composition according to claim 1, wherein said fat is selected from the group consisting of a higher alcohol having a linear or branched $C_{8-24}$ alkyl or alkenyl group, a hydrocarbon oil, a solid paraffin, a lanolin derivative, a higher fatty acid ester having 8 to 24 carbon atoms, a higher fatty acid having 8 to 24 carbon atoms, a polyoxyethylene alkyl ether containing not more than 5 moles of polyoxyethylene, animal fat, animal oil, vegetable fat, vegetable oil, a cholesterol fatty acid ester, diglyceride, triglyceride, and silicon oil, and mixtures thereof.

4. The composition according to claim 1, wherein said nonionic surfactant is selected from the group consisting of a monoglyceride, a glyceryl ether, and a polyether-modified silicone, and mixtures thereof.

5. The composition according to claim 1, wherein said cationic surfactant is selected from the group consisting of a quarternary ammonium salt, a linear alkyl trimethylammonium halide, a linear dialkyl dimethylammonium halide, a branched alkyl trimethylammonium halide, a linear dialkylammonium halide, and a branched dialkyl dimethylammonium halides, and mixtures thereof.

6. The composition according to claim 3, wherein said quaternary ammonium salt comprises a counterion selected from the group consisting of chloride ion, bromide ion and iodide ion.

7. The composition according to claim 1, wherein said hydroxycarboxylic acid is selected from the group consisting of glycolic acid, lactic acid, methyl lactic acid, mandelic acid, 4-hydroxymandelic acid, 3-hydroxy-4-methoxymandelic acid, 4-hydroxy-3-methoxymandelic acid, 3-(2-hydroxyphenyl) lactic acid, 3-(4'-hydroxyphenyl) lactic acid, 3,4-dihydroxymandelic acid, glyceric acid, malic acid, tartaric acid, and citric acid and mixtures thereof.

8. The composition according to claim 1, wherein said dicarboxylic acid is selected from the group consisting of malonic acid, succinic acid, maleic acid, benzoic acid, phthalic acid, salicylic acid, and fumaric acid and mixtures thereof.

9. The composition according to claim 1, wherein a pH of said composition is 2 to 7.

10. A method of preparing a composition, comprising:
combining:
(A) 40 to 98 wt. % of a polyhydric alcohol is selected from the group consisting of ethylene glycol, propylene glycol, 1,2-butylene glycol, 1,3-butylene glycol, 3-methyl-1,3-butylene glycol, dipropylene glycol, hexylene glycol, glycerin, trimethylol propane, pentaerythritol, xylitol, sorbitol, and mannitol and mixtures thereof;
(B) 0.01 to 40% of at least one component, soluble in component (A), selected from the group consisting of a fat, a nonionic surfactant, a cationic surfactant, a higher alcohol, a hydroxycarboxylic acid, a dicarboxylic acid and mixtures thereof;
(C) 0 to 20 wt. % of water; and
(D) 0.3 to 10 wt. % of hydroxypropyl cellulose,
wherein a temperature of said composition rises by at least 2° C. when mixed with the same amount of water having the same initial temperature.

11. A method for treating hair, comprising:
applying a composition comprising:
(A) 40 to 98 wt. % of a polyhydric alcohol is selected from the group consisting of ethylene glycol, propylene glycol, 1,2-butylene glycol, 1,3-butylene glycol, 3-methyl-1,3-butylene glycol, dipropylene glycol, hexylene glycol, glycerin, trimethylol propane, pentaerythritol, xylitol, sorbitol, and mannitol and mixtures thereof;
(B) 0.01 to 40% of at least one component, soluble in component (A), selected from the group consisting of a fat, a nonionic surfactant, a cationic surfactant, a higher alcohol, a hydroxycarboxylic acid, a dicarboxylic acid and mixtures thereof;
(C) 0 to 20 wt. % of water; and
(D) 0.3 to 10 wt. % of hydroxypropyl cellulose to hair,
wherein a temperature of said composition rises by at least 2° C. when mixed with the same amount of water having the same initial temperature.

12. The method for treating hair of claim 4, wherein said composition is rinsed off after application to hair.

* * * * *

UNITED STATES PATENT AND TRADEMARK OFFICE
CERTIFICATE OF CORRECTION

PATENT NO. : 6,607,718 B1
DATED : August 19, 2003
INVENTOR(S) : Mika Okuno et al.

It is certified that error appears in the above-identified patent and that said Letters Patent is hereby corrected as shown below:

Column 5,
Line 61, delete "is"

Column 7,
Line 18, delete "is"

Column 8,
Line 8, delete "is"

Signed and Sealed this

Fourth Day of May, 2004

JON W. DUDAS
*Acting Director of the United States Patent and Trademark Office*